(12) United States Patent
Aferzon et al.

(10) Patent No.: US 8,920,505 B2
(45) Date of Patent: *Dec. 30, 2014

(54) MINIMALLY INVASIVE LATERAL INTERVERTEBRAL FIXATION SYSTEM, DEVICE AND METHOD

(75) Inventors: Joseph Aferzon, Avon, CT (US); Jeffrey A. Bash, West Hartford, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,921

(22) Filed: Feb. 10, 2012

(65) Prior Publication Data

US 2012/0143340 A1 Jun. 7, 2012

Related U.S. Application Data

(63) Continuation of application No. 12/246,946, filed on Oct. 7, 2008, now Pat. No. 8,167,950.

(60) Provisional application No. 60/998,376, filed on Oct. 11, 2007.

(51) Int. Cl.
  *A61F 2/44* (2006.01)
  *A61F 2/46* (2006.01)
  *A61F 2/30* (2006.01)

(52) U.S. Cl.
  CPC ............. *A61F 2/4611* (2013.01); *A61F 2/4455* (2013.01); *A61F 2/447* (2013.01); *A61F 2002/30471* (2013.01); *A61F 2002/30492* (2013.01); *A61F 2002/30515* (2013.01); *A61F 2002/30579* (2013.01); *A61F 2002/30784* (2013.01); *A61F 2002/4627* (2013.01); *A61F 2220/0025* (2013.01); *A61F 2220/0091* (2013.01)
  USPC ..................................... 623/17.16; 623/17.11

(58) Field of Classification Search
  CPC .......... A61F 2/44; A61F 2/4455; A61F 2/447
  USPC ........... 606/246–257, 86 A; 623/17.11–17.16
  See application file for complete search history.

(56) References Cited

U.S. PATENT DOCUMENTS

| 5,254,118 | A | 10/1993 | Mirkovic |
| 5,609,635 | A | 3/1997 | Michelson |
| 5,658,335 | A | 8/1997 | Allen |

(Continued)

FOREIGN PATENT DOCUMENTS

WO 2004080356 A2 4/2009

*Primary Examiner* — Nicholas Woodall
(74) *Attorney, Agent, or Firm* — Hoffmann & Baron, LLP

(57) ABSTRACT

An intervertebral fixation device and system are disclosed, including a weight-bearing shell, first anchor, second anchor, and key. The shell includes a first and second opposing sidewalls, a keyway that extends between and through the first and second sidewalls, and a first axis of rotation and a second axis of rotation that extend between the first and second sidewalls. The first anchor is rotatably coupled to the shell about a first axis of rotation and is disposed in a first orientation. The second anchor is rotatably coupled to the shell about a second axis of rotation and is disposed in a second orientation. The second orientation is divergent from the first orientation. The key is configured to be disposed in the keyway to support the first anchor in a third orientation and the second anchor in a fourth orientation. The third orientation is divergent from the fourth orientation.

25 Claims, 6 Drawing Sheets

(56) References Cited

U.S. PATENT DOCUMENTS

| | | |
|---|---|---|
| 5,800,550 A | 9/1998 | Sertich |
| 6,174,311 B1 * | 1/2001 | Branch et al. ............... 606/86 A |
| 6,371,987 B1 | 4/2002 | Weiland et al. |
| 6,443,990 B1 | 9/2002 | Aebi et al. |
| 6,527,803 B1 | 3/2003 | Crozet et al. |
| 6,767,367 B1 * | 7/2004 | Michelson ................ 623/17.16 |
| 6,770,096 B2 * | 8/2004 | Bolger et al. .............. 623/17.16 |
| 6,923,830 B2 | 8/2005 | Michelson |
| 7,594,932 B2 | 9/2009 | Aferzon et al. |
| 8,070,819 B2 | 12/2011 | Aferzon et al. |
| 8,267,997 B2 * | 9/2012 | Colleran ................... 623/17.11 |
| 2002/0143401 A1 | 10/2002 | Michelson |
| 2003/0187436 A1 | 10/2003 | Bolger et al. |
| 2004/0138672 A1 | 7/2004 | Michelson |
| 2004/0204714 A1 | 10/2004 | Liu et al. |
| 2005/0033429 A1 | 2/2005 | Kuo |
| 2005/0038512 A1 | 2/2005 | Michelson |
| 2006/0142859 A1 * | 6/2006 | McLuen ................... 623/17.11 |
| 2006/0253201 A1 | 11/2006 | McLuen |
| 2007/0270961 A1 * | 11/2007 | Ferguson .................. 623/17.11 |

* cited by examiner

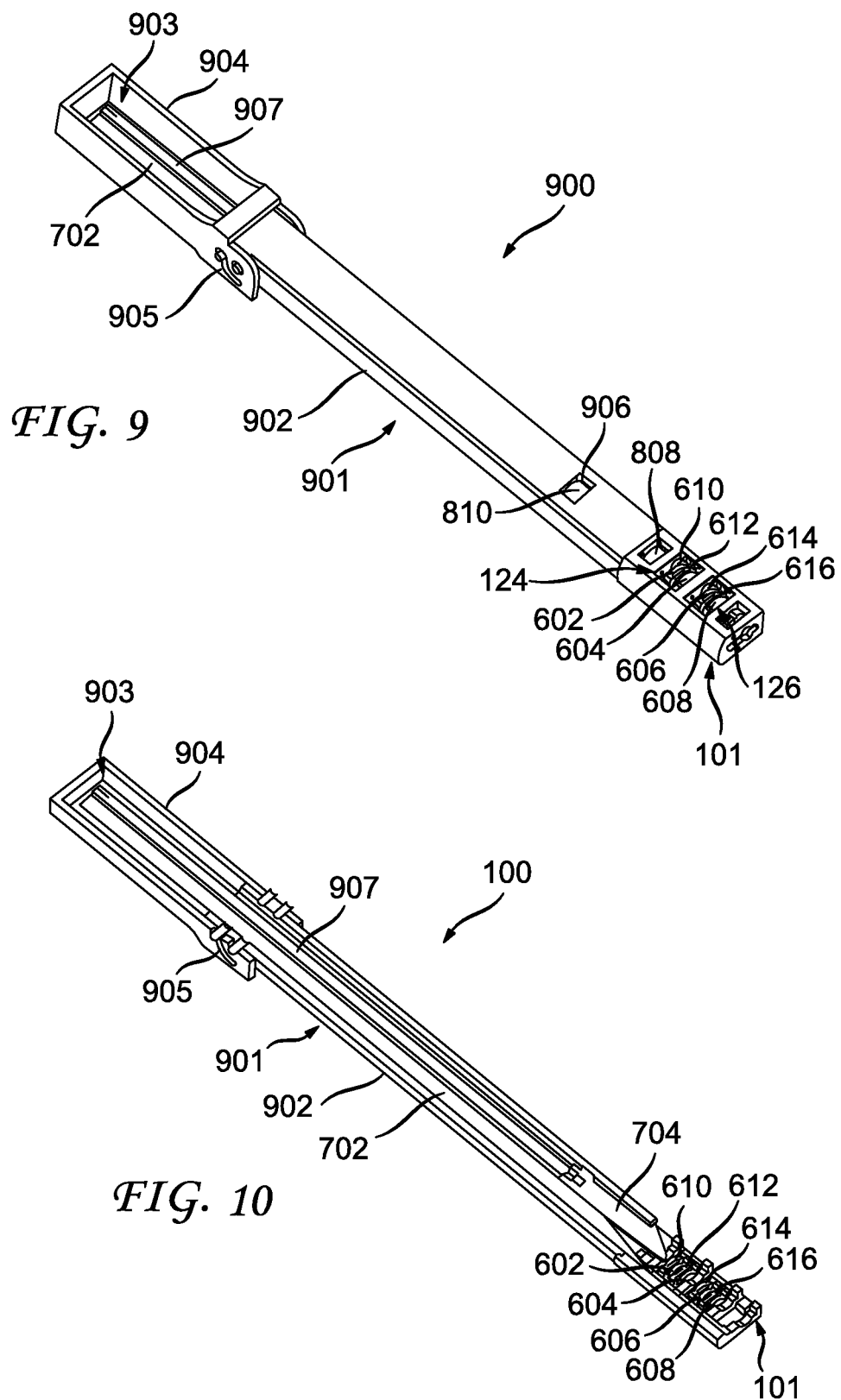

US 8,920,505 B2

MINIMALLY INVASIVE LATERAL INTERVERTEBRAL FIXATION SYSTEM, DEVICE AND METHOD

CROSS-REFERENCE TO RELATED APPLICATIONS

This application is a continuation of U.S. patent application Ser. No. 12/246,946, filed Oct. 7, 2008, which claims priority to U.S. Provisional Patent Application No. 60/998,376, filed Oct. 11, 2007, both of which are incorporated herein by reference in their entireties.

BACKGROUND

1. Field

The present disclosure relates generally to spinal fusion devices. More specifically, example embodiments are directed a minimally invasive lateral intervertebral system, device and method.

2. Brief Discussion of Related Art

Articulations between bony vertebrae of a human spine—such as spinal disks and facet joints—frequently deteriorate with age or trauma and become a source of pain. Spinal disk deterioration causes the spinal disk to lose its normal consistency and volume, which facilitates the spinal disk to collapse and to cause abnormally painful motion across the spinal disk within the spine. The abnormal motion across the deteriorating spinal disk also increases the stresses on the facet joints and accelerates their degeneration, further adding to the abnormally painful motion across the spinal disk of the spine.

A normal spinal disk is a cylindrical weigh-bearing fibrous structure with a non-compressible viscous center. Due to its ability to deform, the spinal disk not only supports normal functional loads of the human body (e.g., load bearing) but also cushions and evenly distributes the stresses applied with body movement and positioning (e.g., load sharing). The spinal disk articulates between the bony vertebrae—one vertebra above the spinal disk and one vertebra below the spinal disk—through large surface area interfaces known as endplates. An endplate is a thin (e.g., 1 mm-3 mm) and approximately round plate (e.g., 2 cm-4 cm in diameter) of dense bone and cartilage accounting for a majority of the vertebral load-bearing capacity.

Surgical treatment of spinal disk disorders has required fusion or elimination of movement across the abnormal spinal disk. This has been accomplished by allowing bone to grow between adjacent vertebrae and through a disk space of the abnormal spinal disk. In the foregoing surgical treatment, the disk space of the abnormal disk is restored to its normal height by opening the disk space occupied by the spinal disk, which is removed, while also restoring a normal curvature of the spine determined by a differential height between the front and the back of the spinal disk between adjacent vertebrae (e.g., lordosis). The foregoing restoration is commonly achieved by using a disk implant that opens the space and allows for growth of bridging bone that fuses the adjacent vertebrae. The ultimate effectiveness of the disk implant is based on: (i) its ability to restore and maintain normal curvature of the spine across the disk space; (ii) ease of its insertion and fixation within the disk space; (iii) its facilitation of bony fusion of the adjacent vertebrae; and (iv) its restriction of movement of the adjacent vertebrae in respect to the disk implant across the disk space.

Disk implants vary in shape but possess similar characteristics with upper and lower surfaces conforming to the shape of the vertebral endplates and vertical designs that aim to restore normal height of the collapsed disk space and to restore normal curvature of spine. The disk implants are sufficiently porous or hollow to allow bridging bone to grow through the disk implants and to bridge the adjacent vertebrae (e.g., bone fusion). These disk implants generally perform well with vertical load bearing and flexion of the spine. However, these disk implants are not able to restrict movement between adjacent vertebrae when the vertebrae are pulled apart, or subjected to extension and lateral bending. These disk implants further provide negligible restriction during translation (e.g., sliding motion) and rotation of the spine.

Some disk implants cut into or have protrusions directed into or through the endplates of the vertebrae. These protrusions penetrate the endplates and potentially create channels for bone growth, yet do not alter structural properties of the endplates. These protrusions further reduce the risk of extrusion of the disk implants from of the disk space. The protrusions restrict translation of the disk implants but the protrusions do not restrict extension and lateral bending. This necessitates additional fixation or immobilization usually via posterior pedicle screws.

One of the surgical techniques used to deliver the disk implant is a minimally invasive lateral approach. The minimally invasive lateral approach utilizes a tubular access retractor to remove the spinal disk and to deliver a weight-bearing disk implant. The disk implant delivered via the lateral approach does not provide sufficiently rigid fixation and requires a further surgical procedure to provide posterior fixation of the disk implant. A current solution is to utilize a lateral plate secured with two screws. The lateral plate requires repetitive delivery of multiple components through a small channel and provides a relatively small fixation advantage over the standalone disk implant. The ability to provide sufficient fixation across the disk space through the minimally invasive lateral approach would eliminate the second surgical procedure.

SUMMARY

In a particular embodiment, an intervertebral fixation device is disclosed. The device includes a weight-bearing shell, first anchor, second anchor and key. The weight-bearing shell includes a first and second opposing sidewalls, a keyway that extends between and through the first and second opposing sidewalls, and a first axis of rotation and a second axis of rotation that extend between the first and second opposing sidewalls.

The first anchor is rotatably coupled to the weight-bearing shell about a first axis of rotation and is disposed in a first orientation in relation to the weight-bearing shell. The second anchor is rotatably coupled to the weight-bearing shell about a second axis of rotation and is disposed in a second orientation in relation to the weight-bearing shell. The second orientation is divergent from the first orientation.

The key is configured to be disposed in the keyway to support the first anchor in a third orientation in relation to the weight-bearing shell and the second anchor in a fourth orientation in relation to the weight-bearing shell, the third orientation divergent from the fourth orientation.

In another particular embodiment, an intervertebral fixation system is disclosed. The intervertebral fixation system includes an intervertebral fixation device. The intervertebral fixation device includes a weight-bearing shell, first anchor, second anchor and key. The weight-bearing shell includes a first and second opposing sidewalls, a keyway that extends between and through the first and second opposing sidewalls, and a first axis of rotation and a second axis of rotation that extend between the first and second opposing sidewalls.

The first anchor is rotatably coupled to the weight-bearing shell about a first axis of rotation and is disposed in a first orientation in relation to the weight-bearing shell. The second anchor is rotatably coupled to the weight-bearing shell about a second axis of rotation and is disposed in a second orientation in relation to the weight-bearing shell. The second orientation is divergent from the first orientation.

The key is configured to be disposed in the keyway to support the first anchor in a third orientation in relation to the weight-bearing shell and the second anchor in a fourth orientation in relation to the weight-bearing shell, the third orientation divergent from the fourth orientation.

Other aspects, advantages, and features of the present disclosure will become apparent after review of the entire application, including the following sections: Brief Description of the Drawings, Detailed Description, and the Claims.

BRIEF DESCRIPTION OF THE DRAWINGS

FIG. 9 is a perspective view of a second embodiment of a minimally invasive lateral intervertebral system;

FIG. 10 is a perspective view of a cross-section of the second embodiment of the minimally invasive lateral intervertebral system of FIG. 9;

DETAILED DESCRIPTION

Figure 1:
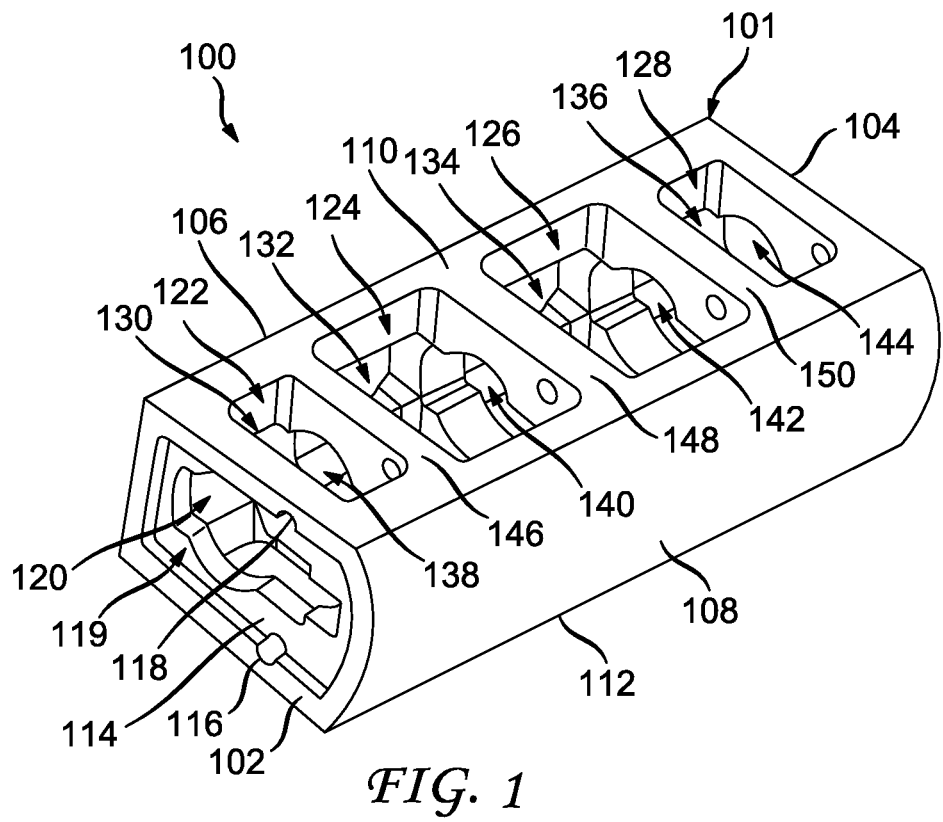
FIG. 1 is a perspective view of an example shell of a minimally invasive lateral intervertebral fixation device.

FIG. 1 is a perspective view 100 of an example shell 101 of a minimally invasive lateral intervertebral fixation device. The minimally invasive lateral intervertebral fixation device is illustrated in and described with reference to FIG. 11. The shell 101 is made of a material, such as a thermoplastic, a polymer, or a composite thereof, that is sufficiently resilient to withstand stress or pressure of bodily movement and positioning, while providing a degree of elasticity and also providing biostablity and biocompatibility. The material should have a modulus of elasticity that is comparable to bone. For example, the shell 101 may be made of polyetheretherketone (PEEK), a thermoplastic with a Young's modulus of elasticity of about 3.6 GPa and a tensile strength of about 90 MPa. Also, because PEEK is resistant to both organic and aqueous environments, it is practical for the minimally invasive lateral intervertebral fixation device. Other materials that may be used include metals, ceramics, medical plastics, coral, and other medically applicable materials.

In various embodiments, the dimensions of the shell 101 are approximately the following: the length of the shell 101 between sidewalls 102, 104 is between about 45 mm and about 55 mm; the width of the shell 101 between the back wall 106 and the front wall 108 is between about 15 mm to about 22 mm; and the height of the shell between top and bottom surfaces 110, 122 is between about 8 mm and about 14 mm. It is noted that the foregoing dimensions are non-limiting and may be appropriately adjusted depending on different levels of the spine (e.g., cervical, lumbar, thoracic) and depending on a particular person's spinal anatomy.

The shell 101 includes sidewalls 102, 104, intermediate walls 146, 148 and 150 between the sidewalls 102, 104, a back wall 106, a front wall 108, and top and bottom surfaces 110, 112. One or more of the sidewalls 102, 104 include a depression or a recess 114 to interface with an introducer described herein below with reference to FIGS. 9 and 10. As is described in reference to FIGS. 9 and 10, the introducer includes a reciprocal protrusion to pressure fit the depression or recess 114 of the shell 101. While the sidewalls 102, 104, the intermediate walls 146, 148, 150 and the top and bottom surfaces 110, 112 are generally flat surfaces, the front wall 108 is a generally curve-shaped or arcuate surface. The sidewalls 102, 104 and the intermediate walls 146, 148, 150 include through holes 116 and 118 aligned at about the top and bottom surfaces 110, 112, forming respective lengthwise channels through the shell 101 to receive and secure to the shell 101 plural anchors (shown in FIG. 4) by using respective pins (not shown) inserted through the respective channels. The respective lengthwise channels through the shell 101 provide respective axes of rotation proximate to the top and bottom surfaces 110, 112 of the shell 101. The through holes 116, 118 are disposed proximate to the bottom and the top of the sidewalls 102, 104 and the intermediate walls 146, 148, 150. The sidewalls 102, 104 and the intermediate walls 146, 148, 150 also include respective key-shaped openings 120, 138, 140, 142, 144 (hereinafter collectively referred to as a "keyway opening" or "keyway" 119) that provide access to the plural anchors (shown in FIG. 6) to enable their rotation from a concealed position within the shell 101 into an extended and fixed position in relation to the shell 101 (shown in FIG. 1 I), using a wedge and a cylindrical key (shown in FIGS. 7, 8 and 10). Each of the key-shaped openings 120, 138, 140, 142, 144 is shaped identically to form the keyway opening or keyway 119 between and through the sidewalls 102, 104.

The shell 101 includes plural openings 122, 124, 126 and 128 through the top and bottom surfaces 110, 112, plural openings 130, 132, 134 and 136 through the back wall 106 and the keyway opening 119 (e.g., plural key-shaped openings 120, 138, 140, 142 and 144) between and through the sidewalls 102, 104. Openings 122, 128 are about 5 mm-6 mm by about 10 mm-12 mm, and openings 124, 126 are about 10 mm-12 mm by about 12 mm-16 mm. Openings 130, 132, 134 and 136 may be of various sizes. The foregoing plural openings form or define plural chambers (e.g., four chambers) within the shell 101 to facilitate growth of bridging bone through the shell 101 of the minimally invasive lateral intervertebral fixation device. The inner chambers (e.g., innermost two chambers), as indicated by the openings 124, 126, also conceal plural anchors as illustrated in and described in reference to FIGS. 4-6. The outer chambers, as indicated by openings 122 and 128 do not conceal any anchors and facilitate locking of the cylindrical key (shown in FIGS. 7, 8 and 10).

Figure 2:
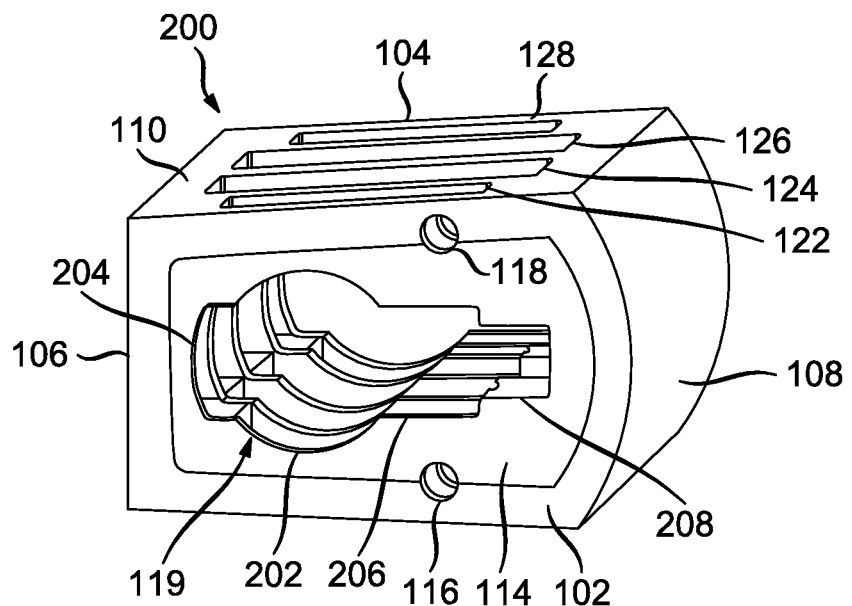
FIG. 2 is an elevated side view of the example shell of FIG. 1.

FIG. 2 is an elevated side view 200 of the example shell 101 of FIG. 1. The keyway 119 (e.g., each of the key-shaped openings 120, 138, 140, 142, 144) includes four portions 202, 204, 206 and 208. A central approximately round portion 202 approximates the circumference of the cylindrical key of FIG. 8, while portion 204 approximates the dimension of plural protrusions about the circumference of the cylindrical key of FIG. 8. Portions 202 and 204 allow the cylindrical key to move through the keyway 119 when the protrusions are aligned with portion 204 and restrict movement of the cylindrical key when the protrusions of the cylindrical key are not aligned with portion 204. Portions 202, 204, 206 and 208 of the keyway 119 facilitate access to and rotation of the plural anchors concealed within the shell 101 (shown in FIG. 6) from their concealed position within the shell 101 into an extended and fixed position in relation to the shell 101 (shown in FIG. 11), using the wedge and the cylindrical key (shown in FIGS. 7, 8 and 10).

Figure 3:
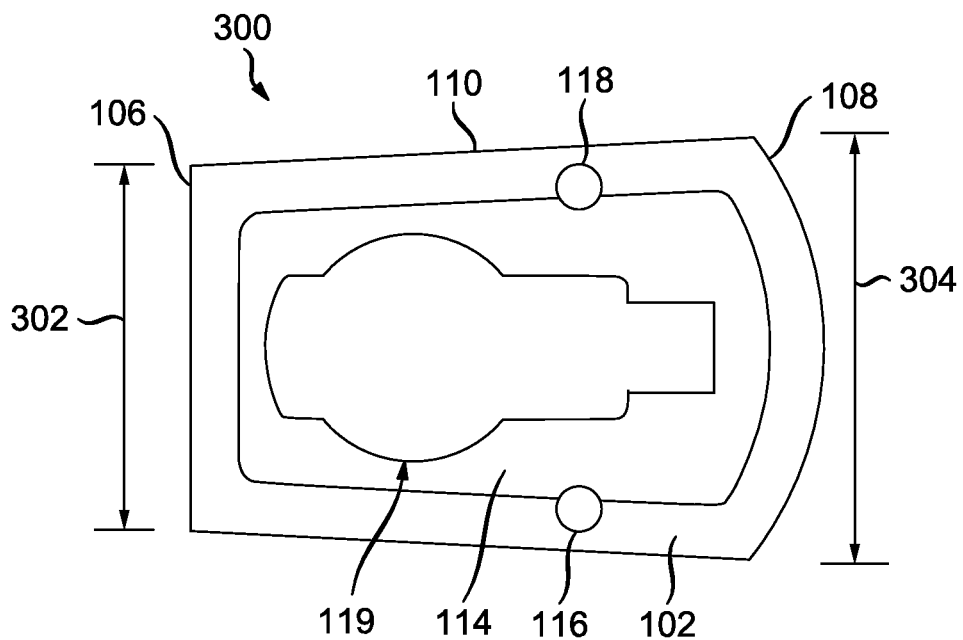
FIG. 3 is a side view of the example shell of FIG. 1.

FIG. 3 is a side view 300 of the example shell 101 of FIG. 1. As illustrated in the side view 300, the sidewalls 102, 104 and the intermediate walls 146, 148, 150 gradually increase in height from the back wall 106 to the front wall 108, where the top and bottom surfaces 110, 112 are angled with respect to a horizontal plane through a center of the shell 101 (not shown) from the back wall 106 to the front wall 108. To illustrate, in a particular embodiment, the shell 101 of the minimally invasive lateral intervertebral fixation device has a front height 304 of the front wall 108 that is higher than a back height 302 in the back wall 106 to provide for a natural curvature of the cervical or lumbar segments of the spine into which the minimally invasive lateral intervertebral fixation device may be implanted. The difference between the heights 302, 304 may be from about 2 mm to about 3 mm. In an example embodiment, the back height 302 may be about 10 mm and the front height 304 may be about 12 mm. The heights 302, 304 may also be equal. As such, the angle may be varied (adjusting the heights 302, 304) between different levels of the spine (e.g., cervical, lumbar, thoracic) and between different people. The angle between the top surface 110 and the horizontal plane (or the bottom surface 112 and the horizontal plane) may be between zero (0) and six (6) degrees, while a combined angle between the horizontal plane and top and bottom surfaces 110, 112 will most commonly be between three (3) and six (6) degrees depending on the level of the spine and a particular person's spinal anatomy.

Figure 4:
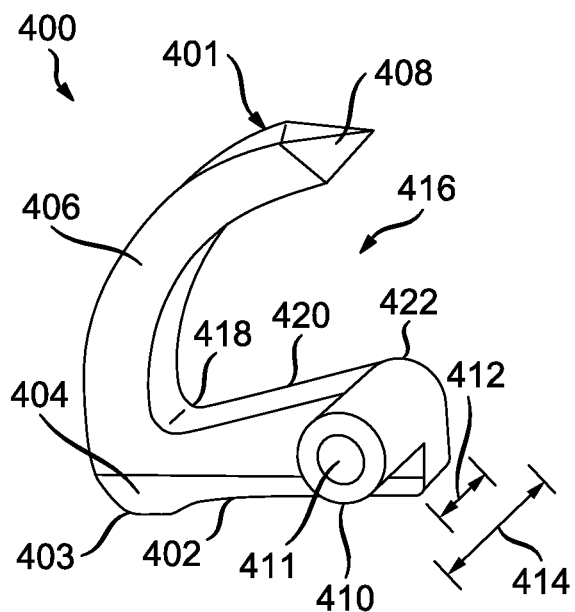
FIG. 4 is an elevated view of an example anchor of the minimally invasive lateral intervertebral fixation device.

FIG. 4 is an elevated view 400 of an example anchor 401 of the minimally invasive lateral intervertebral fixation device. In a particular embodiment, the anchor 401 is made of a metal, such as titanium. Other medically applicable metals may be employed. The anchor 401 is generally c-shaped, having a generally straight base portion 402 that has a protrusion 403, which provides a pivot for rotating the anchor 401 with the wedge and the cylindrical key of FIGS. 7, 8 and 10. Additionally, the protrusion 403 is of a shape that approximates an edge of portion 202 of the key-shaped openings 120, 138, 140, 142, 144 so that the cylindrical key better restricts the rotational movement of the anchor 401. The base portion 402 includes a beveled or chamfered edge 404 to facilitate the wedge in more easily advancing by and rotating the anchor 401. A projection or arm portion 406 extends in a curve-shaped or arcuate direction from the base portion 402 and is adapted to secure an endplate of a vertebra of the spine. The projection 406 includes a leading pointed or sharp edge 408 adapted to penetrate the endplate of a vertebra of the spine. A cylinder portion 410 is disposed transverse to the base portion 402. The cylinder portion 410 includes through hole 411 to secure the anchor 401 in the shell 101 (via pins described above inserted via through holes 116 or 118 and via through hole 411) and to facilitate the anchor 401 in rotating about the axis of rotation at the top or the bottom surfaces 110, 122 of the shell 101 via through hole 411. In a particular embodiment, the through hole 411 is approximately 1.5 mm and the projection 406 is a curve or arc that is approximately 10 mm from the center of the through hole 411. The width 412 of the base portion 402 is about half of the length 414 of the cylinder portion 410. In a particular embodiment, the width 412 is approximately 2.5 mm, the length 414 is approximately 5.5 mm, and the height of the anchor 401 from the base portion 402 to sharp edge 408 is about 12.5 mm. As is described in detail below, an inner surface 416 of the anchor 401 is of a shape that generally approximates the surface 110 or surface 112 of the shell 101 to provide weight-bearing support for the endplate of the vertebra that it will engage. The inner surface 416 may be adjusted to approximate the surface 110 or surface 112 of the shell 101. The inner surface 416 includes a top edge 422 of the cylinder portion 410 that transitions to a flat edge 420 of the base portion 402 and includes a continuous inclining edge 418 that transitions the flat edge 420 to the arcuate projection or arm 406.

Figure 5:
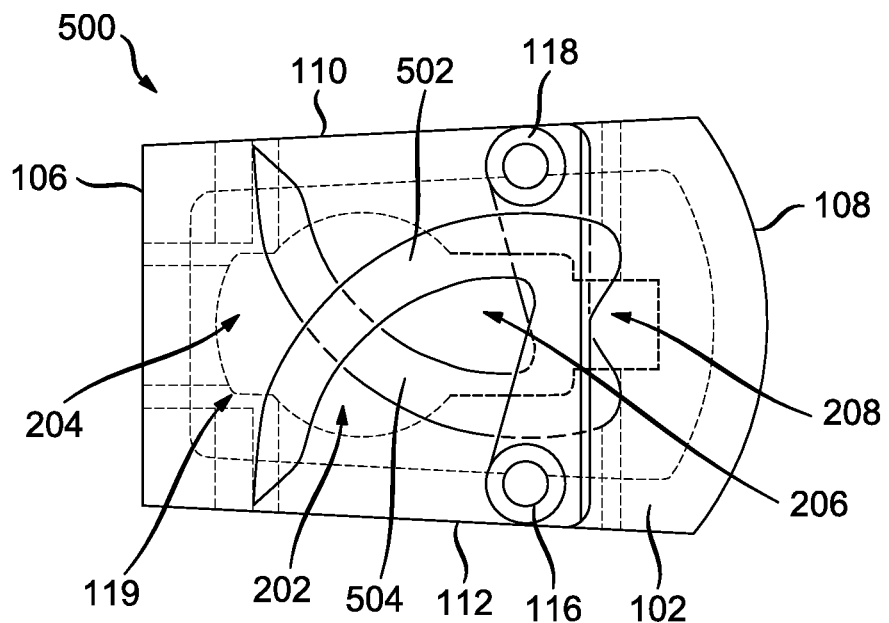
FIG. 5 is a side translucent view of the example shell of FIG. 1 with plural example anchors concealed within the shell of FIG. 1.

FIG. 5 is a side translucent view 500 of the example shell 101 of FIG. 1 with plural example anchors 502, 504 concealed within the shell 101. A first anchor of the plural anchors 502 is positioned in a first orientation and a second anchor 504 is positioned in a second orientation in relation to the first anchor 502. More specifically, the second anchor 504 is positioned upside down in relation to the first anchor 502. The disparate orientations of the anchors 502, 504 in relation to one another enables the anchors 502, 504 to diverge through the openings 124, 126 in the top and bottom surfaces 110, 112 and to engage with endplates of respective vertebra of the spine (not shown). The disparate orientations of the anchors 502, 504 also facilitate the wedge and the cylindrical key of FIGS. 7, 8 and 10 to be inserted through portions 202, 204, 206 and 208, to engage the anchors 502, 504 with the endplates of the respective vertebrae and to lock the anchors 502, 504 in relation to the shell 101 and the respective vertebrae.

Figure 6:
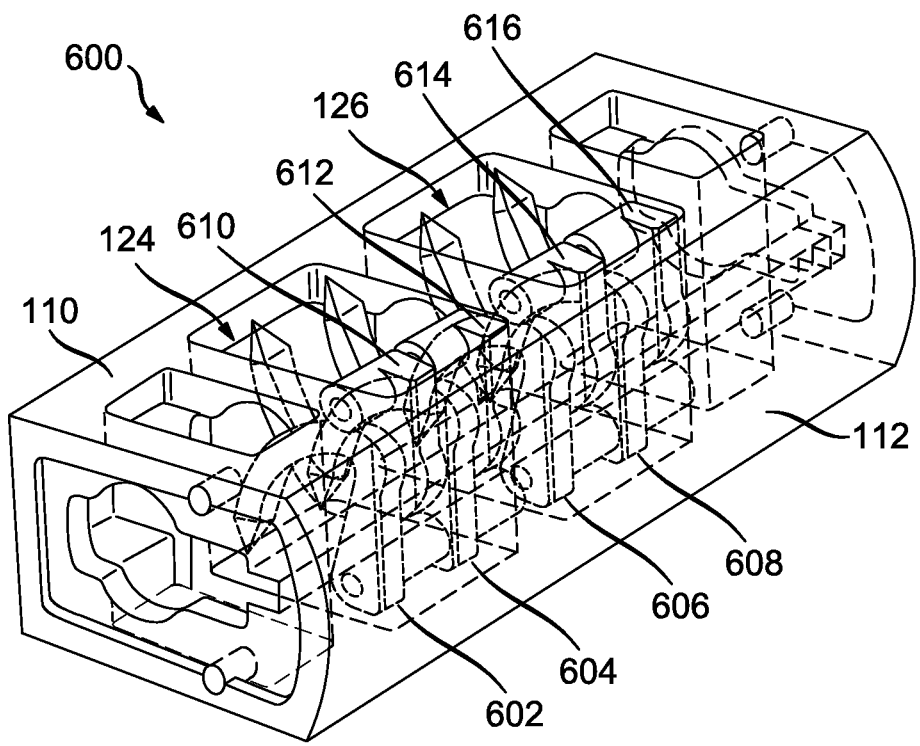
FIG. 6 is a perspective translucent view of the shell of FIG. 1 with plural preloaded anchors in a concealed position within the shell of FIG. 1.

FIG. 6 is a perspective translucent view 600 of the shell 101 of FIG. 1 with plural preloaded anchors 602-616 in a concealed position within the shell 101. The shell 101 conceals four (4) sets of disparately oriented anchors (602, 610), (604, 612), (606, 614), and (608, 616). As illustrated in view 600, the length of the cylinder portion of each anchor 602-616 (e.g., length 414 in FIG. 4) is approximately double of the width of the base portion (e.g., width 412 in FIG. 4) of each anchor 602-616. This allows sufficient width of the cylinder to secure the anchors 602-616 to the shell 101 when the anchors 602-616 are extended (shown in FIG. 11), while mitigating the amount of space necessary for the anchors 602-616. Anchors (602, 610) and (604, 612) diverge and extend through openings 124 in the top and bottom surfaces 110, 112, while anchors (606, 614) and (608, 616) diverge and extend through openings 126 in the top and bottom surfaces 110, 112.

Figure 7:
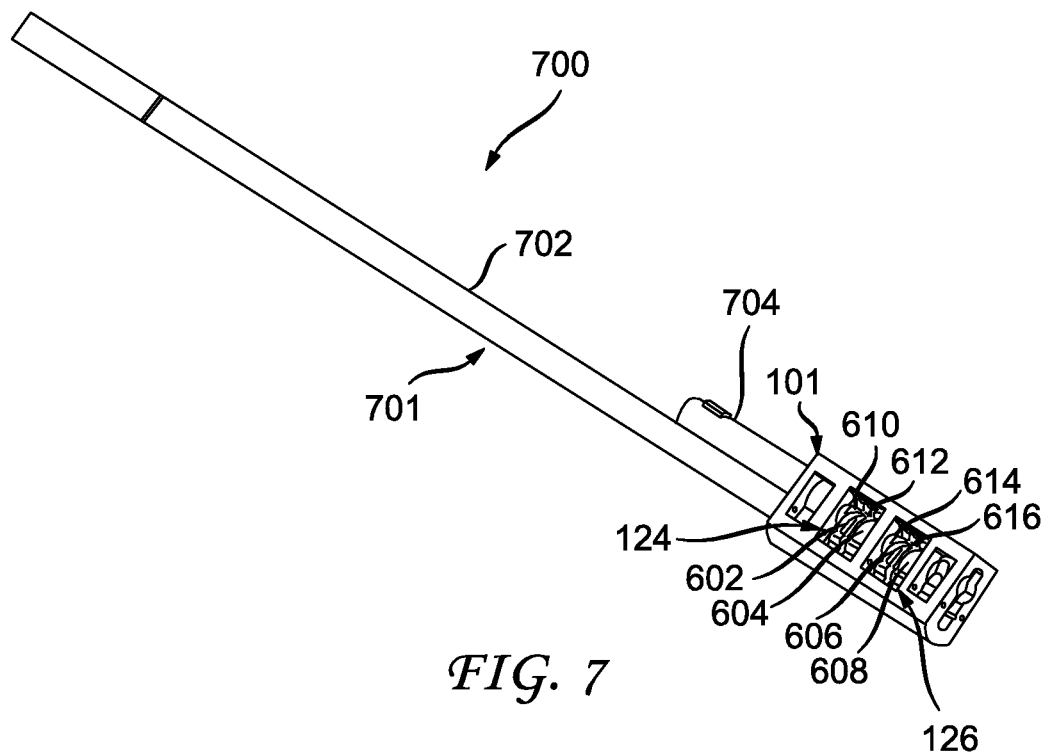
FIG. 7 is a perspective view of a first embodiment of a minimally invasive lateral intervertebral system.

FIG. 7 is a perspective view 700 of a first embodiment of a minimally invasive lateral intervertebral system 701. The minimally invasive lateral intervertebral system 701 includes an example wedge 702 and an example cylindrical key 704 to interface with the example shell 101 and the example plural anchors 602-616. The wedge 702 and cylindrical key 704 are used to rotate the respective sets of anchors (602, 610), (604, 612), (606, 614), and (608, 616), in order from the proximal to the distal, from a concealed position within the shell 101 into an extended and fixed position in relation to the shell 101 (shown in FIG. 11) to engage and secure endplates of respective vertebrae (not shown). For example, the wedge 702 is advanced forward (e.g., via portions 206 and 208 of the keyway 119) to rotate a first proximal set of anchors (602, 610) from the concealed position within the shell 101 to an intermediately rotated position in which the base portions of the set of anchors (e.g., base portion 402 of FIG. 4) are disposed within the central portion (e.g., central portion 202 of FIG. 2) of the keyway 119 (e.g., key-shaped opening 138 of FIG. 1). The wedge is similarly advanced from the sidewall 102 to the sidewall 104 to rotate the respective sets of the anchors into intermediately rotated positions. In the intermediately rotated position, the respective sets of anchors have been partially extended from the shell 101 through the openings (e.g., openings 124, 126 of FIG. 1) in the top and bottom surfaces of shell 101 (e.g., top and bottom surfaces 110, 112). The cylindrical key 704 is then advanced forward, fully rotating the first proximal set of anchors (602, 610) and other sets of anchors (604, 612), (606, 614), and (608, 616) into their fully extended positions in relation to the shell 101.

Figure 8:
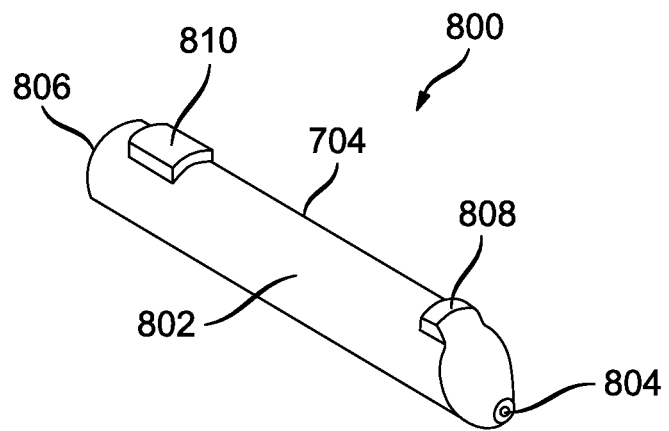
FIG. 8 is a perspective view of an example cylindrical key of minimally invasive lateral intervertebral system of FIG. 7.

FIG. 8 is a perspective view 800 of the example cylindrical key 704 of the minimally invasive lateral intervertebral system of FIG. 7. The cylindrical key 704 is made of a solid material, such as PEEK, to provide the same biomechanical properties (e.g., resilience and elasticity) as the shell 101. The cylindrical key 704 includes a cylinder portion 802 that includes a driving/rotating end 806 and a conical end 804. The driving/rotating end 806 includes a slit (shown in FIGS. 10-12) for a driver (not shown) that can drive and rotate the cylindrical key 704. The conical end 804 is offset from the center of the cylinder portion's 802 diameter to more easily rotate the anchors from the intermediately rotated position to a fully extended position. The cylindrical key 704 further includes protrusions 808 and 810 that facilitate the cylindrical key 704 to be driven forward when the protrusions 808, 810 are in a first orientation (e.g., protrusions 808, 810 aligned with portion 204 of the keyway 119 shown in FIGS. 1 and 2). The protrusions further facilitate the cylindrical key 704 to secure the respective sets of anchors (e.g., 602-616 of FIG. 6) when the protrusions 808, 810 are rotated via the driving/rotating end 812 into a second orientation. More specifically, protrusion 810 may be engaged between sidewall 102 and intermediate wall 146, while protrusion 810 may be engaged by intermediate wall 150, to support the sets of anchors (e.g., 602-616 of FIG. 6) in extended positions relative to the shell 101 and to prevent the cylindrical key 704 from dislodging from the shell 101. In a particular embodiment, the length of the cylindrical key 704 is about 50 mm and its cross-sectional diameter is about 8 mm. In this embodiment, the protrusions 808, 810 have a height of about 1.5 mm from the surface of the cylindrical key 704, where the protrusion 810 has a length of about 6 mm and a width of about 5 mm, and the protrusion 808 has a length of about 2 mm and a width of about 5 mm. In this embodiment, the protrusion 808 includes a chambered or a beveled edge that forms a part of the conical end 804.

FIG. 9 is a perspective view of a second embodiment of a minimally invasive lateral intervertebral system 900. The minimally invasive lateral intervertebral system 900 includes an example introducer 901, the shell 101 with plural anchors 602-616, the wedge 702, the cylindrical key 704 (shown in FIG. 10) and an extender/connector 907. The introducer 901 interfaces with the shell 101 and the cylindrical key 704 to deliver and implant the shell 101, the plural anchors 602-616 and the cylindrical key 704 (e.g., the minimally invasive lateral intervertebral fixation device) into a disk space between plural vertebrae.

The introducer 901 is made of a rigid radiolucent material, such as a radiolucent metal. In various embodiments, the radiolucent metal may be aluminium, beryllium or other radiolucent metal. In a particular embodiment, the introducer 901 is approximately 20 cm long and has a hollow configuration that approximates the shell 101 shown in FIG. 1. The introducer includes a mating protrusion that pressure fits the depression or recess 114 of the shell 101. The introducer 901 includes a handle portion 902 and a swivel portion 904. To facilitate the minimally invasive lateral approach in delivering the minimally invasive lateral intervertebral fixation device (shown in FIG. 11), the plural anchors 602-616 are preloaded within the shell 101, and the wedge 702 and the cylindrical key 704 are preloaded with the introducer 901. Also preloaded into the introducer 901 is the extender/connector 907 that interfaces the cylindrical key 704 to a driving/rotating tool (not shown), such as hexagonal screwdriver, to facilitate the cylindrical key's 704 advancement and rotation in the shell 101 via the driving/rotating end 806 of the cylindrical key 704. More specifically, the access to the cylindrical key 704 may be extended by the extender/connector 907, which may include a driving/rotating end and a mating end that fits the driving/rotating end 806 of the cylindrical key 704.

The handle portion 902 includes an opening 906 that receives protrusion 810 of the cylindrical key 704, while the shell 101 receives the protrusion 808 via opening 122 between sidewall 102 and intermediate wall 146 (shown in FIG. 1). Thus, the cylindrical key 704 temporarily secures the introducer 901 to the shell 101 to facilitate the delivery of the shell 101, the anchors 602-616 concealed therein, the cylindrical key 704 and the extender/connector 907 into the disk space between the vertebrae (not shown). The swivel portion 904 includes a pivoting mechanism 905 that allows the swivel portion 904 to pivot via the pivoting mechanism 905 at about 90 degrees with respect to the handle portion 902. Striking a hammer on the swivel portion 904 that is inline with respect to the handle portion 902 is used to deliver or advance the shell 101, the plural concealed anchors 602-616 and the cylindrical key 706 into position within the disk space between the vertebrae.

The swivel portion 904 includes an opening 903 that provides access to the preloaded wedge 702 and the cylindrical key 704 via the extender/connector 907. More specifically, after positioning the shell 101 in a proper orientation within the disk space by using the introducer 901 in its inline position (e.g., the swivel portion 904 is extended in line with the handle portion 902 as shown in FIG. 9), the swivel portion 904 is pivoted (not shown) via the pivoting mechanism 905 to expose the wedge 704 and the extender/connector 907 to the cylindrical key 704 via the opening 903. The wedge 702 is advanced forward into the shell 101 to rotate the anchors 602-616 into their respective intermediately rotated positions. The cylindrical key 704 is then rotated about 90 degrees via the driving/rotating end 806 by using the extender/connector 907, until protrusions 808, 810 coincide with portion 204 of the keyway 119 (shown in FIG. 2), thereby unlocking the cylindrical key 704 from the introducer 901. The cylindrical key 704 is advanced via the extender/connector 907 into the shell 101, rotating the anchors 602-616 into their respective final extended positions. The cylindrical key 704 is then locked in the shell 101 by rotating the cylindrical key 704 via the extender/connector 907 back or forward so that the protrusions 808, 810 do not coincide with portion 204 of the keyway 119. The wedge 702 and the extender/connector 907 are removed and the introducer 901 is removed from the disk space. Thus, the shell 101 is secured to the endplates of the vertebrae via the anchors 602-616 and the cylindrical key 704.

FIG. 10 is a perspective view 1000 of a cross-section of the second embodiment of a minimally invasive lateral intervertebral system 900 of FIG. 9. Perspective view 1000 illustrates cross-sections of the example introducer 901 that interfaces with the example shell 101 and the cylindrical key 704 to deliver and implant the shell 101, the plural anchors 602-616 and the cylindrical key 704 (e.g., minimally invasive lateral intervertebral fixation device). The perspective view 1000 also illustrates the preloaded anchors 602-616 in the shell 101, the preloaded wedge 702, cylindrical key 704 and extender/connector 907 within the introducer 901. The preloading of the foregoing elements via the shell 101 and the introducer 901 facilitates the minimally invasive lateral approach in delivering and securing the minimally invasive lateral intervertebral fixation device (e.g., shell 101, anchors 602-616, cylindrical key 704) within the disk space between vertebrae.

Figure 11:
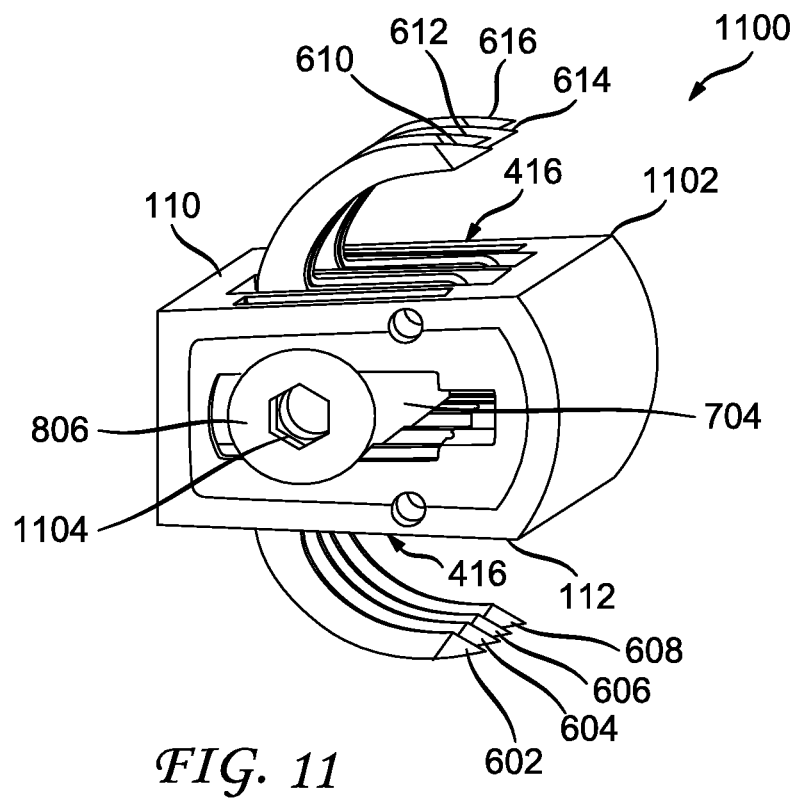
FIG. 11 is an elevated side view of a minimally invasive lateral intervertebral fixation device.

FIG. 11 is an elevated side view 1100 of a minimally invasive lateral intervertebral fixation device 1102. The minimally invasive lateral intervertebral fixation device 1102 is shown with plural anchors 602-616 of FIG. 6 in an extended position in relation to the shell 101 of FIG. 1. The plural anchors 602-616 are locked via the cylindrical key 704, which may be advanced via the driving/rotating end 806 and rotated via a hexagonal recess 1104. In the extended and locked position, the base portions of the plural anchors 602-616 (e.g., base portion 402) are supported by the cylindrical key 704. The inner surfaces 416 of the plural anchors 602-616 generally approximate the surfaces 110 or 112 to provide weight-bearing support for the endplates of the vertebrae.

Figure 12:
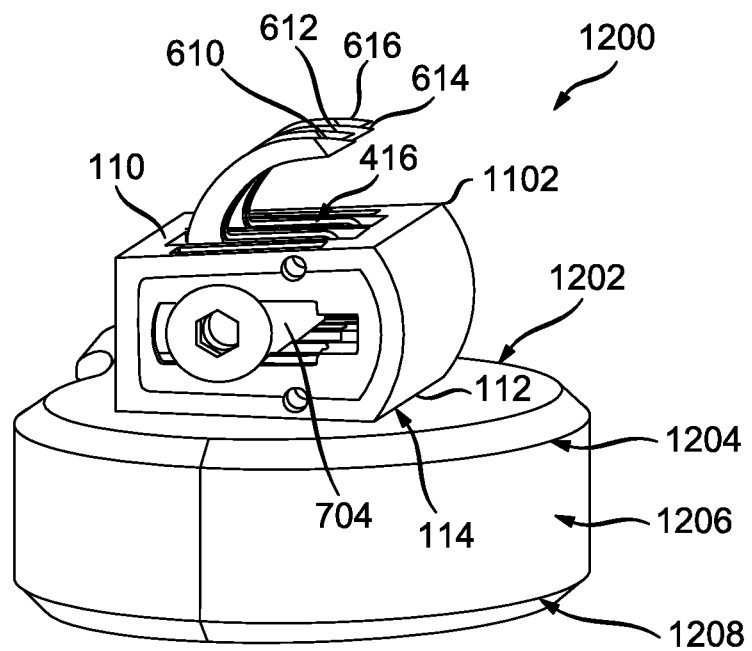
FIG. 12 is an elevated side view of the minimally invasive lateral intervertebral fixation device of FIG. 11 with the plural example anchors in a locked and an extended position in relation to the shell of FIG. 1 and securing a top endplate of a vertebra of a spine.

FIG. 12 is an elevated side view 1200 of the minimally invasive lateral intervertebral fixation device 1102 of FIG. 11 with the plural example anchors 602-616 in a locked and an extended position in relation to the shell of FIG. 1 and securing a top endplate 1204 of a vertebra 1202 of a spine (not shown). For clarity, the minimally invasive lateral intervertebral fixation device 1102 is shown securing only one vertebra. It is noted, however, that the minimally invasive lateral intervertebral fixation device 1102 is inserted into a disk space between plural vertebrae, one below and one on top of the minimally invasive lateral intervertebral fixation device 1102, and secures the plural vertebrae via the respective anchors 602-608 and 610-616 and cylindrical key 704. The minimally invasive lateral intervertebral fixation device 1102 is disposed approximately centrally within the disk space between the plural vertebrae. The vertebra 1202 includes a top endplate 1204, a bottom endplate 1208 and a central portion 1206. The endplates 1204, 1208 consist of cortical bone, which is much harder and denser than the cancellous bone of the central portion 1206. Consequently, the respective anchors 602-608 and 610-616 hook and secure the respective endplates 1204 and 1208 of plural vertebrae. The inner surfaces 416 of the plural anchors 602-608 and 610-616 generally approximate the top surface 110 or the bottom surface 112 to provide weight-bearing support for the endplates of the vertebra. Because the shell 101 and the cylindrical key 704 are made of the same material (e.g., PEEK) and the inner surfaces 416 of the plural anchors 602-608 and 610-616 approximate the top and bottom surfaces 110, 112 of the shell 101, the minimally invasive lateral intervertebral fixation device 1102 provides substantial weight-bearing capability and mitigates subsidence of the of the minimally invasive lateral intervertebral fixation device 1102 into the vertebrae.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

What is claimed is:

1. An intervertebral fixation device, the device comprising:
    a weight-bearing shell including a first and second opposing sidewalls, a keyway that extends from and through a first opposing sidewall to and through a second opposing sidewall of the first and second opposing sidewalls, and a first axis of rotation and a different second axis of rotation that are outside the keyway and extend from the first opposing sidewall to the second opposing sidewall of the first and second opposing sidewalls;
    a first anchor rotatably coupled to the weight-bearing shell about the first axis of rotation and disposed in a first orientation in relation to the weight-bearing shell;
    a second anchor rotatably coupled to the weight-bearing shell about the second axis of rotation and disposed in a second orientation in relation to the weight-bearing shell, the second orientation divergent from the first orientation; and
    a key configured to be locked in the keyway supporting the first anchor in a third orientation in relation to the weight-bearing shell and the second anchor in a fourth orientation in relation to the weight-bearing shell, the third orientation divergent from the fourth orientation.

2. The intervertebral fixation device of claim 1, wherein the first anchor includes an inner surface that approximates a top surface of the weight-bearing shell when supported by the key, the top surface extending between the first and second opposing sidewalls.

3. The intervertebral fixation device of claim 1, wherein the second anchor includes an inner surface that approximates a bottom surface of the weight-bearing shell when supported by the key, the bottom surface extending between the first and second opposing sidewalls.

4. The intervertebral fixation device of claim 1, wherein the first axis of rotation extends proximate to a top surface of the weight-bearing shell, the top surface extending between the first and second opposing sidewalls.

5. The intervertebral fixation device of claim 1, wherein the second axis of rotation extends proximate to a bottom surface of the weight-bearing shell, the bottom surface extending between the first and second opposing sidewalls.

6. The intervertebral fixation device of claim 1, wherein at least one anchor of the first anchor and the second anchor comprises:
    a base portion configured to be supported by the key in relation to the weight-bearing shell;
    an arm portion that extends in a curve-shaped direction from the base portion and is configured to penetrate and secure to a first vertebra or a second vertebra; and
    a cylinder portion disposed transversely to the base portion and configured to facilitate the at least one anchor in rotating about the first axis of rotation or the second axis of rotation.

7. The intervertebral fixation device of claim 6, wherein the base portion comprises an inner surface that approximates a top surface of the weight-bearing shell or a bottom surface of the weight-bearing shell when supported by the key.

8. The intervertebral fixation device of claim 6, wherein the cylinder portion comprises a through hole to rotatably secure the at least one anchor in relation to the weight-bearing shell via a pin that extends along the first axis of rotation or the second axis of rotation.

9. The intervertebral fixation device of claim 1, wherein the first anchor rotates about the first axis of rotation through an opening in a top surface of the weight-bearing shell to the third orientation in relation to the weight-bearing shell as the key is advanced in the keyway.

10. The intervertebral fixation device of claim 1, wherein the second anchor rotates about the second axis of rotation through an opening in a bottom surface of the weight-bearing shell to the fourth orientation in relation to the weight-bearing shell as the key is advanced in the keyway.

11. The intervertebral fixation device of claim 1, wherein the key includes a cylindrical body, plural protrusions extending from the cylindrical body to lock the key in the weight-bearing shell, and a conical end to facilitate rotation of the first anchor and the second anchor.

12. The intervertebral fixation device of claim 11, wherein the keyway includes a cylindrical first portion configured to receive the cylindrical body of the key and a second portion configured to receive the plural protrusions of the key as the key is advanced in the keyway.

13. An intervertebral fixation system, the system comprising:
   an intervertebral fixation device, the device including:
      a weight-bearing shell including a first and second opposing sidewalls, a keyway that extends from and through a first opposing sidewall to and through a second opposing sidewall of the first and second opposing sidewalls, and a first axis of rotation and a different second axis of rotation that are outside the keyway and that extend from the first opposing sidewall to the second opposing sidewall of the first and second opposing sidewalls;
      a first anchor rotatably coupled to the weight-bearing shell about the first axis of rotation and disposed in a first orientation in relation to the weight-bearing shell;
      a second anchor rotatably coupled to the weight-bearing shell about the second axis of rotation and disposed in a second orientation in relation to the weight-bearing shell, the second orientation divergent from the first orientation; and
      a key configured to be locked in the keyway supporting the first anchor in a third orientation in relation to the weight-bearing shell and the second anchor in the fourth orientation in relation to the weight-bearing shell, the third orientation divergent from the fourth orientation.

14. The intervertebral fixation system of claim 13, wherein the system comprises a wedge to rotate the first anchor about the first axis through an opening in a top surface of the weight-bearing shell from the first orientation in relation to the weight-bearing shell to an intermediate orientation in relation to the weight-bearing shell.

15. The intervertebral fixation system of claim 14, wherein the first anchor rotates from the intermediate orientation to the third orientation in relation to the weight-bearing shell as the key is advanced in the keyway.

16. The intervertebral fixation system of claim 13, wherein the system comprises a wedge further configured to rotate the second anchor about the second axis through an opening in a bottom surface of the weight-bearing shell from the second orientation in relation to the weight-bearing shell to an intermediate orientation in relation to the weight-bearing shell.

17. The intervertebral fixation system of claim 16, wherein the second anchor rotates from the intermediate orientation in relation to the weight-bearing shell to the fourth orientation in relation to the weight-bearing shell as the key is advanced in the keyway.

18. The intervertebral fixation system of claim 13, wherein the system comprises an extender to interface the key to a driving/rotating tool.

19. The intervertebral fixation system of claim 13, wherein the system comprises an introducer that interfaces the intervertebral fixation device to insert the intervertebral fixation device into a disk space between plural vertebrae.

20. The intervertebral fixation system of claim 19, wherein the introducer includes a handle portion that has an opening to receive a first protrusion of the key and the weight-bearing shell includes an opening to receive a second protrusion of the key to removeably lock the introducer to the weight-bearing shell using the key.

21. The intervertebral fixation system of claim 19, wherein the introducer includes a swivel portion configured to pivot in relation to the handle portion.

22. The intervertebral fixation system of claim 19, wherein the system comprises a wedge that is preloaded into the introducer, the wedge disposed proximately to the first anchor and the second anchor.

23. The intervertebral fixation system of claim 19, wherein the system comprises an extender that is preloaded into the introducer, the extender engaging the key.

24. The intervertebral fixation system of claim 23, wherein the system comprises a screw driving/rotating tool configured to engage the extender to unlock the key from the introducer, the screw driving/rotating tool engaged to the extender further configured to advance the key in the keyway to rotate the first anchor and the second anchor in relation to the weight-bearing shell.

25. The intervertebral fixation system of claim 23, wherein the screw driving/rotating tool engaged to the extender is further configured to lock the key in the weight-bearing shell.

* * * * *